United States Patent
Seki et al.

(10) Patent No.: US 8,642,820 B2
(45) Date of Patent: Feb. 4, 2014

(54) PROCESS FOR PRODUCING 1,1-DICHLORO-2,3,3,3-ETRAFLUOROPROPENE AND 2,3,3,3-TETRAFLUOROPROPENE

(75) Inventors: Ryuji Seki, Tokyo (JP); Hidekazu Okamoto, Tokyo (JP); Hirokazu Takagi, Tokyo (JP); Satoshi Kawaguchi, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 240 days.

(21) Appl. No.: 13/167,285

(22) Filed: Jun. 23, 2011

(65) Prior Publication Data

US 2011/0319678 A1 Dec. 29, 2011

Related U.S. Application Data

(60) Provisional application No. 61/365,895, filed on Jul. 20, 2010.

(30) Foreign Application Priority Data

Jun. 23, 2010 (JP) ................................. 2010-142279

(51) Int. Cl.
*C07C 17/10* (2006.01)
(52) U.S. Cl.
USPC ............................ 570/176; 570/151; 570/156
(58) Field of Classification Search
None
See application file for complete search history.

(56) References Cited

U.S. PATENT DOCUMENTS

| 5,157,171 A * | 10/1992 | Sievert et al. | 570/151 |
| 6,548,719 B1 * | 4/2003 | Nair et al. | 570/157 |
| 8,293,953 B2 * | 10/2012 | Okamoto | 570/151 |
| 2010/0022808 A1 | 1/2010 | Rao et al. | |
| 2010/0145111 A1 * | 6/2010 | Sharratt et al. | 570/156 |

FOREIGN PATENT DOCUMENTS

| JP | 8-169850 | | 7/1996 |
| JP | 08169850 A | * | 7/1996 |
| JP | 3778298 | | 5/2006 |
| JP | 2010-510221 | | 4/2010 |
| JP | 2010-513437 | | 4/2010 |
| WO | WO 2008060614 A2 | * | 5/2008 |
| WO | WO 2009/125201 A2 | | 10/2009 |
| WO | WO 2010/013576 A1 | | 2/2010 |

OTHER PUBLICATIONS

International Search Report issued on Sep. 6, 2011 in PCT/JP2011/064422 (with Translation of Category of Cited Documents).
U.S. Appl. No. 13/167,464, filed Jun. 23, 2011, Takagi, et al.
U.S. Appl. No. 13/167,455, filed Jun. 23, 2011, Okamoto.
U.S. Appl. No. 13/167,235, filed Jun. 23, 2011, Kawaguchi, et al.
U.S. Appl. No. 13/167,509, filed Jun. 23, 2011, Kawaguchi, et al.
U.S. Appl. No. 13/167,145, filed Jun. 23, 2011, Takagi, et al.
U.S. Appl. No. 13/167,254, filed Jun. 23, 2011, Kawaguchi, et al.
Paul Tarrant, Fluorine Chemistry Reviews, vol. 8, pp. 39-71, 1967.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide a process to produce 1,1-dichloro-2,3,3,3-tetrafluoropropene (CFO-1214ya) simply and economically without requiring purification of 1,1-dichloro-2,2,3,3,3-pentafluoropropane (HCFC-225ca) from the raw material component obtained as a mixture of isomers, i.e. dichloropentafluoropropane (HCFC-225) including HCFC-225ca and at the same time to produce simply and economically 2,3,3,3-tetrafluoropropene (HFO-1234yf) from 1-chloro-2,3,3,3-tetrafluoropropane (HCFC-244eb).

A raw material composition comprising HCFC-244eb and HCFC-225 including HCFC-225ca is contacted with an alkali aqueous solution in the presence of a phase-transfer catalyst to produce CFO-1214ya from HCFC-225ca and at the same time to produce HFO-1234yf from HCFC-244eb.

12 Claims, 1 Drawing Sheet

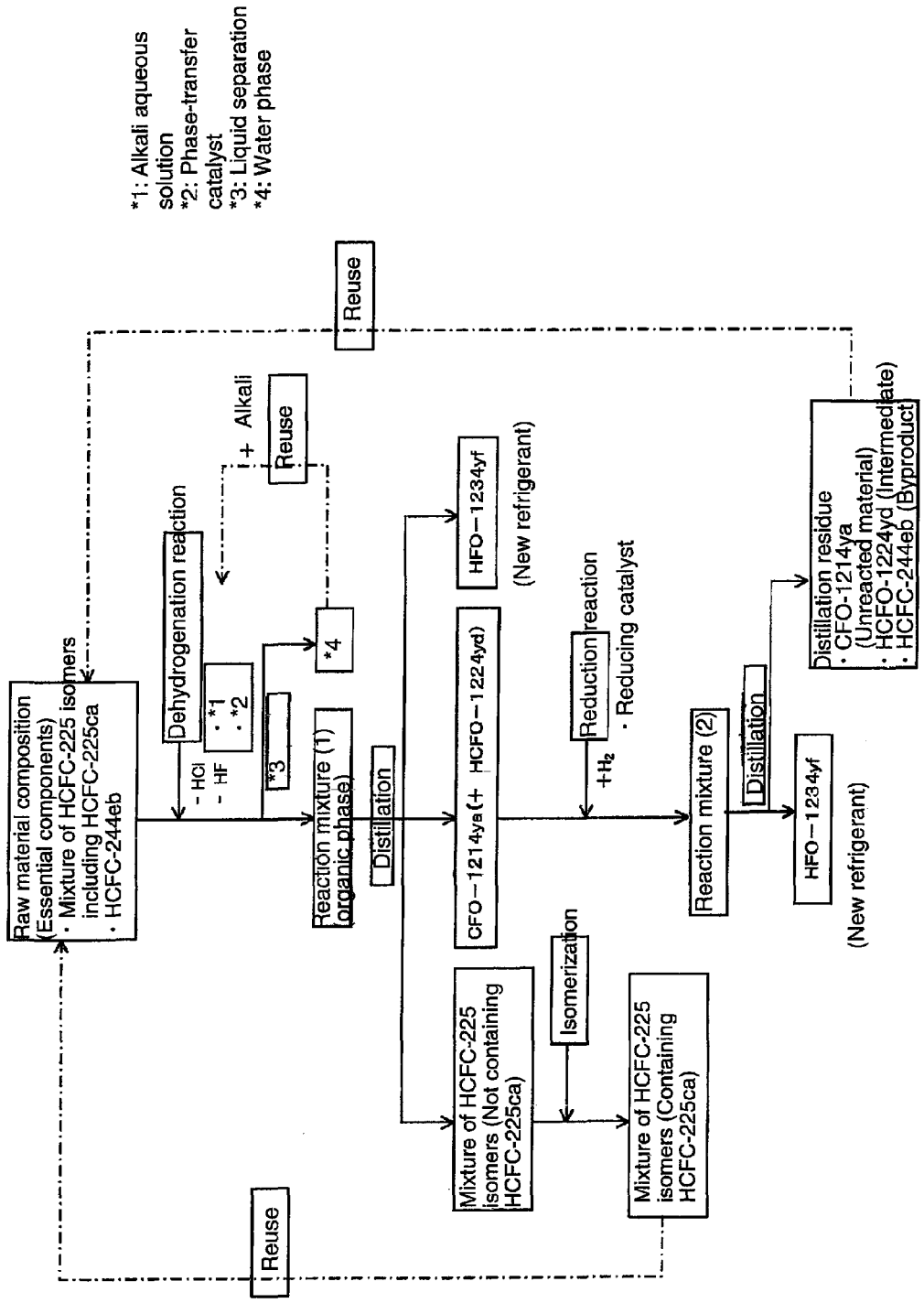

PROCESS FOR PRODUCING 1,1-DICHLORO-2,3,3,3-ETRAFLUOROPROPENE AND 2,3,3,3-TETRAFLUOROPROPENE

TECHNICAL FIELD

The present invention relates to a process for producing 1,1-dichloro-2,3,3,3-tetrafluoropropene and 2,3,3,3-tetrafluoropropene.

BACKGROUND ART 1,1-Dichloro-2,3,3,3-tetrafluoropropene (CFO-1214ya) is a compound useful as a raw material for synthesis of 2,3,3,3-tetrafluoropropene (HFO-1234yf) which is expected in recent years as a new refrigerant to replace 1,1,1,2-tetrafluoroethane (HFC-134a) being a greenhouse effect gas. In this specification, with respect to a halogenated hydrocarbon, in brackets after the chemical name, an abbreviation of the compound is indicated, but in this specification, instead of the compound name, its abbreviation may be employed as the case requires.

As a method for producing such CFO-1214ya, a method has been known wherein 1,1-dichloro-2,2,3,3,3-pentafluoropropane (HCFC-225ca) is, as a production raw material, dehydrofluorinated in an alkali aqueous solution in the presence of a phase-transfer catalyst or in a gas phase reaction in the presence of a catalyst such as chromium, iron, copper or activated carbon (Patent Document 1).

Here, HCFC-225ca to be used as the production raw material in the above method is usually produced as a mixture of 1,3-dichloro-1,2,2,3,3-pentafluoropropane (HCFC-225cb), 2,2-dichloro-1,1,3,3,3-pentafluoropropane (HCFC-225aa) and other isomers (Patent Document 2, Non-Patent Document 1). Therefore, it has been separated from such a mixture of isomers and purified to be used as a raw material for the above production method.

However, in such a mixture of dichloropentafluoropropane isomers, the respective isomers have boiling points close to one another, whereby it is difficult to separate and purify them by a usual separation/purification technique (such as distillation), and a multi-stage distillation or the like is required to produce highly pure HCFC-225ca on an industrial scale.

When the production including preparation of the production raw material, etc. is comprehensively taken into account in such a manner, the above-mentioned conventional method for producing CFO-1214ya is hardly regarded as a simple and economical production method.

On the other hand, CFO-1214ya obtained by such a method can be converted to HFO-1234yf by reducing it with hydrogen in the presence of a catalyst.

In such a reduction reaction, an outlet gas of the reduction reactor contains, in addition to the desired product HFO-1234yf, an unreacted raw material CFO-1214ya, an intermediate product 1-chloro-2,3,3,3-tetrafluoropropene (HCFO-1224yd) and byproducts such as 1-chloro-2,3,3,3-tetrafluoropropane (HCFC-244eb), etc.

Here, the unreacted raw material CFO-1214ya and the intermediate product HCFO-1224yd can be effectively utilized by recycling them to the reduction reactor after separating them by distillation from the desired product HFO-1234yf.

However, a byproduct HCFC-244eb has a boiling point close to CFO-1214ya and HCFO-1224yd and can hardly be separated by distillation from these compounds. HCFC-244eb is returned to the reduction reactor together with CFO-1214ya and HCFO-1224yd, but since it is an inactive compound in the reduction reaction, there has been a problem that as the operation of returning it to the reduction reactor is repeated, it is concentrated in the reduction reactor thereby to lower the production efficiency of HFO-1234yf.

PRIOR ART DOCUMENTS

Patent Documents

Patent Document 1: Japanese Patent No. 3,778,298
Patent Document 2: U.S. Pat. No. 5,157,171

Non-Patent Document(s)

Non-Patent Document 1: "Fluorine Chemistry Reviews, Vol. 8", p. 39-71, compiled by Paul Tarrant, published by MARCEL DEKKER, INC. in 1967

DISCLOSURE OF INVENTION

Technical Problem

The present invention has been made from the above viewpoints, and it is an object of the present invention to provide a process for producing CFO-1214ya simply and economically without requiring purification of the raw material component obtained as a mixture of isomers i.e. HCFC-225ca and for simply and economically producing HFO-1234yf useful as a new refrigerant from HCFC-244eb which has been considered to have low usefulness.

Further, it is another object of the present invention to provide a process for producing HFO-1234yf useful as a new refrigerant from the CFO-1214ya obtained as described above.

Solution to Problem

The process for producing tetrafluoropropenes of the present invention comprises contacting a raw material composition comprising 1-chloro-2,3,3,3-tetrafluoropropane (HCFC-244eb) and dichloropentafluoropropane including 1,1-dichloro-2,2,3,3,3-pentafluoropropane (HCFC-225ca) and at least one of its isomers, with an alkali aqueous solution in the presence of a phase-transfer catalyst, to produce 1,1-dichloro-2,3,3,3-tetrafluoropropene (CFO-1214ya) from the 1,1-dichloro-2,2,3,3,3-pentafluoropropane (HCFC-225ca), and to produce 2,3,3,3-tetrafluoropropene 1234yf) from the 1-chloro-2,3,3,3-tetrafluoropropane (HCFC-244eb).

Further, the process for producing 2,3,3,3-tetrafluoropropene (HFO-1234yf) of the present invention comprises separating 1,1-dichloro-2,3,3,3-tetrafluoropropene (CFO-1214ya) and 2,3,3,3-tetrafluoropropene (HFO-1234yf), respectively, from the reaction product obtainable by the above process for producing tetrafluoropropenes, and reacting the separated 1,1-dichloro-2,3,3,3-tetrafluoropropene (CFO-1214ya) with hydrogen in the presence of a catalyst to produce 2,3,3,3-tetrafluoropropene (HFO-1234yf).

Further, the present invention provides a process for producing 2,3,3,3-tetrafluoropropene (HFO-1234yf) characterized by the following combination of steps.

A process for producing 2,3,3,3-tetrafluoropropene (HFO-1234yf), which comprises:

a hydrogenation step of reacting 1,1-dichloro-2,3,3,3-tetrafluoropropene (CFO-1214ya) with hydrogen in the presence of a catalyst to produce 2,3,3,3-tetrafluoropropene (HFO-1234yf), which is separated from the reaction product, and to obtain a mixture comprising unreacted 1,1-dichloro-2,3,3,3-tetrafluoropropene (CFO-1214ya), 1-chloro-2,3,3,3- tetrafluoropropene (HCFO-1224yd) as an intermediate product and 1-chloro-2,3,3,3-tetrafluoropropane (HCFC-244eb) as a by-product;

a mixing step of mixing dichloropentafluoropropane including 1,1-dichloro-2,2,3,3,3-pentafluoropropane (HCFC-225ca) and at least one of its isomers, and the above mixture obtained in the above hydrogenation step, to obtain a raw material composition comprising 1,1-dichloro-2,2,3,3,3-pentafluoropropane (HCFC-225ca) and 1-chloro-2,3,3,3-tetrafluoropropane (HCFC-244eb); and a dehydrohalogenation step of contacting the raw material composition with an alkali aqueous solution in the presence of a phase-transfer catalyst to produce 1,1-dichloro-2,3,3,3-tetrafluoropropene (CFO-1214ya) from the 1,1-dichloro-2,2,3,3,3-pentafluoropropane (HCFC-225ca) and to produce 2,3,3,3-tetrafluoropropene (HFO-1234yf) from the 1-chloro-2,3,3,3-tetrafluoropropane (HCFC-244eb), and separating the 1,1-dichloro-2,3,3,3-tetrafluoropene (CFO-1214ya) and the 2,3,3,3-tetrafluoropropene (HFO-1234yf), respectively, from the reaction product;

wherein the 1,1-dichloro-2,3,3,3-tetrafluoropropene (CFO-1214ya) separated in the dehydrohalogenation step, is used as at least a part of the 1,1-dichloro-2,3,3,3-tetrafluoropropene (CFO-1214ya) in the hydrogenation step.

Advantageous Effects of Invention

According to the production process of the present invention, it is possible to produce CFO-1214ya simply and economically by using the raw material component obtained as a mixture of isomers i.e. without requiring purification of HCFC-225ca, and at the same time, to simply and economically produce HFO-1234yf useful as a new refrigerant from HCFC-244eb.

Further, by using the CFO-1214ya obtained by such a process, it becomes possible to economically produce HFO-1234yf useful as a new refrigerant.

BRIEF DESCRIPTION OF DRAWING

FIG. 1 is a diagram showing a flowchart for the production of HFO-1234yf utilizing the production process of the present invention.

DESCRIPTION OF EMBODIMENT

Now, an embodiment of the present invention will be described.

In the present invention, "dichloropentafluoropropane" (which is referred to also as HCFC-225) is meant for one of compounds represented by $C_3HCl_2F_5$ or a mixture of two or more of them (i.e. a mixture of compounds which are isomers to one another).

Further, one composed solely of a specific compound X represented by $C_3HCl_2F_5$, or a mixture composed of the compound X and at least one of its isomers, will be referred to as dichloropentafluoropropane (HCFC-225) "inducing a compound X". However, in this specification, unless otherwise specified, "dichloropentafluoropropane (HCFC-225) including a compound X" means a mixture comprising a compound X and at least one of its isomers.

<Process for Producing Tetrafluoropropenes>

The present invention provides a process for producing tetrafluoropropenes, which comprises contacting a raw material composition comprising, as raw material components, HCFC-244eb and HCFC-225 including HCFC-225ca and at least one of its isomers (hereinafter referred to as "HCFC-225 including HCFC-225ca"), with an alkali aqueous solution in the presence of a phase transfer catalyst, to dehydrofluorinate said HCFC-225ca thereby to obtain CFO-1214ya and to dehydrochlorinate said HCFC-244eb thereby to obtain HFO-1234yf. This production process is a process for concurrently producing CFO-1214ya and HFO-1234yf and will hereinafter be referred to as "the concurrent production process of the present invention", as the case requires.

(1) Raw Material Composition

The raw material composition to be used for the concurrently production process of the present invention, comprises HCFC-244eb and HCFC-225 including HCFC-225ca.

(1-1) HCFC-225 Including HCFC-225ca

The above HCFC-225 including HCFC-225ca to be used in the present invention is HCFC-225 comprising HCFC-225ca and at least one of its isomers.

The isomers of HCFC-225ca are not particularly limited, but specifically, they may, for example, be 1,3-dichloro-1,2,2,3,3-pentafluoropropane ($CHClFCF_2CClF_2$, HCFC-225cb), 2,2-dichloro-1,1,3,3,3-pentafluoropropane ($CHF_2CCl_2CF_3$, HCFC-225aa), 1,2-dichloro-1,2,3,3,3-pentafluoropropane ($CHClFCClFCF_3$, HCFC-225ba) and 2,3-dichloro-1,1,2,3,3-pentafluoropropane ($CHF_2CClFCClF_2$, HCFC-225bb). HCFC-225 including HCFC-225ca to be used in the present invention is one composed of one or more of them and HCFC-225ca.

The content ratio of HCFC-225ca in HCFC-225 including HCFC-225ca to be used in the present invention, is not particularly limited, but from the viewpoint of the reactor efficiency, it is preferably at least 10 mol %, more preferably at least 30 mol %, particularly preferably at least 50 mol %. On the other hand, from the viewpoint of the efficiency for separation and purification of HCFC-225ca from an industrial product of HCFC-225, the content ratio of HCFC-225ca in HCFC-225 is preferably at most 99.5 mol %, more preferably at most 90 mol %.

Further, in the raw material composition to be used for the concurrent production process of the present invention, the content of the above HCFC-225 including HCFC-225ca is preferably from 10 to 99.5 mass %, more preferably from 40 to 95 mass %, based on the total amount of the raw material composition, from the viewpoint of the reactor efficiency.

Further, as the above HCFC-225 including HCFC-225ca to be contained in the raw material composition to be used in the present invention, it is possible to employ HCFC-225 obtained as follows.

Firstly, dichloropentafluoropropane (HCFC-225) is usually produced by reacting tetrafluoroethylene and dichlorofluoromethane in the presence of a catalyst as shown by the following reaction formula (1), but HCFC-225 obtained by this reaction is not formed as a compound having a single-structure, but is formed as a mixture of two or more compounds which are in a relationship of isomers to one another.

[Reaction to form HCFC-225]

$$CF_2=CF_2+CHCl_2F \rightarrow C_3HCl_2F_5 (HCFC-225) \quad (1)$$

With respect to HCFC-225 to be obtained by the reaction shown by the above reaction formula (1), the types and proportions of compounds in a relationship of isomers to one another constituting it vary depending upon the reaction conditions, particularly upon the type of the catalyst to be used. However, in most cases, such HCFC-225 contains HCFC-225ca and thus is HCFC-225 including HCFC-225ca which may be used for the process of the present invention.

More specifically, for example, among reactions shown by the above reaction formula (1), in a commonly employed reaction wherein aluminium chloride is used as a catalyst, HCFC-225 thereby obtainable is one which contains mainly HCFC-225ca and HCFC-225cb as reaction products. In such HCFC-225, a small amount of other isomers such as HCFC-225aa, HCFC-225bb, etc. may be contained.

As HCFC-225 to be incorporated to the raw material composition in the concurrent production process of the present invention, it is possible to use HCFC-225 obtainable by a reaction route other than the one shown by the above reaction formula (1), so long as it is HCFC-225 including HCFC-225ca.

Thus, HCFC-225 including HCFC-225ca to be incorporated to the above raw material composition, is formed. In the present invention, it is preferred that HCFC-225 including HCFC-225ca is separated from the reaction product obtained in each of the above-mentioned methods and purified for use.

As HCFC-225, a commercially available one may, for example, be ASAHIKLIN AK-225 (tradename, manufactured by Asahi Glass Company, Limited comprising 48 mol % of HCFC-225ca and 52 mol % of HCFC-225cb).

(1-2) HCFC-244eb

The raw material composition for the concurrent production process of the present invention contains HCFC-244eb together with the above HCFC-225 including HCFC-225ca.

In the concurrent production process of the present invention, CFO-1214ya is produced from HCFC-225ca in the raw material composition, and concurrently, HFO-1234yf is produced from HCFC-244eb. The content ratio of HCFC-244eb to the above HCFC-225 including HCFC-225ca in the raw material composition is not particularly limited so long as it is a content ratio not to impair the respective reactions at the time of producing CFO-1214ya and HFO-1234yf, respectively, by the process of the present invention, and it is preferably from 0.01 to 20 parts by mass, more preferably from 0.1 to 10 parts by mass, as the amount of HCFC-244eb to 100 parts by mass of the above HCFC-225.

HCFC-244eb to be incorporated to the above raw material composition may be incorporated in a state where HCFC-244eb is alone or in a state where it is mixed with other components not to impair the effects of the present invention. From the usefulness of the concurrent production process of the present invention, it is preferred that HCFC-244eb is converted to HFO-1234yf and then taken out.

In the present invention, a mixture containing such HCFC-244eb may be brought in as one obtained from another reaction system. However, it is preferred to use a mixture containing HCFC-244eb obtained as a byproduct in a reaction system to produce HFO-1234yf from CFO-1214ya as described in the above background art. Specifically, the mixture containing HCFC-244eb is preferably a distillation residue obtained by separating HFO-1234yf by distillation from the reaction mixture obtained by reacting CFO-1214ya with hydrogen in the presence of a catalyst.

Such a distillation residue usually contains, in addition to HCFC-244eb as a byproduct, an unreacted raw material CFO-1214ya, an intermediate product HCFO-1224yd, etc. CFO-1214ya and HCFO-1224yd do not hinder the concurrent production process of the present invention, although it may depend also on the contained amounts. Therefore, the above distillation residue may be incorporated, as it is, to the raw material composition.

Further, the above distillation residue may contain, in addition to the above-mentioned various compounds, HCFC-225 including at least one of HCFC-225ca, HCFC-225cb, HCFC-225aa, etc. Also in such a case, the distillation residue may be incorporated, as it is, to the raw material composition. In such a case, the composition of the entire raw material composition is calculated by adding HCFC-225 contained in the distillation residue to HCFC-225 including HCFC-225ca contained in the above raw material composition.

Further, it is preferred to use, as the above-mentioned distillation residue, a distillation residue obtained by separating HFO-1234yf by distillation from the reaction mixture obtained by reacting CFO-1214ya obtained by the concurrent production process of the present invention as a starting material, with hydrogen in the presence of a catalyst, by the after-mentioned process, whereby it becomes possible to effectively use the raw material compounds and byproducts by recycling in a series of reaction systems to produce HFO-1234yf.

Here, in the concurrent production process of the present invention, the above raw material composition may contain, as the case requires, organic compounds other than those described above, within a range not to impair the effects of the present invention. Specifically, the organic compounds which may be contained in the above raw material composition may, for example, be chloroform, chlorodifluoromethane, trifluorooctane, 1,1,3-trichloro-2,2,3,3-tetrafluoropropane, etc. and their content is preferably less than 10 mass % based on the entire amount of the raw material composition.

(2) Production of CFO-1214ya and HFO-1234yf

The concurrent production process of the present invention is one characterized by contacting the above raw material composition with an alkali aqueous solution in the presence of a phase-transfer catalyst, to selectively dehydrofluorinate HCFC-225ca in the raw material composition to obtain CFO-1214ya as shown by the following reaction formula (2), and to dehydrochlorinate HCFC-244eb to obtain HFO-1234yf as shown by the following reaction formula (3).

[Reaction to form CFO-1214ya]

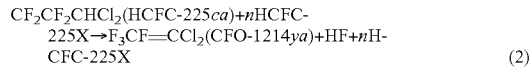

$$CF_2CF_2CHCl_2(HCFC\text{-}225ca)+n HCFC\text{-}225X \rightarrow F_3CF=CCl_2(CFO\text{-}1214ya)+HF+n HCFC\text{-}225X \quad (2)$$

In the reaction formula (2), HCFC-225X represents HCFC-225 other than HCFC-225ca, n represents a molar amount of HCFC-225X per 1 mol of HCFC-225ca in the raw material HCFC-225 and is a numeral larger than 0, and n is preferably from 0.005 to 9.

[Reaction to form HFO-1234yf]

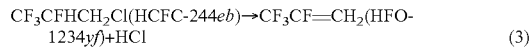

$$CF_3CFHCH_2Cl(HCFC\text{-}244eb) \rightarrow CF_3CF=CH_2(HFO\text{-}1234yf)+HCl \quad (3)$$

Here, in the reaction represented by the above reaction formula (2) wherein HCFC-225ca is selectively dehydrofluorinated, a reaction wherein HCFC-225X undergoes a dehydrofluorination reaction to form an isomer of CFO-1214ya (a compound other than CFO-1214ya among compounds represented by $C_3Cl_2F_4$) may be contained, if it is a minor amount as compared with the reaction amount wherein HCFC-225ca is dehydrofluorinated. Hereinafter, in this specification, the reaction of the reaction formula (2) will be described as it contains the reaction wherein such a minor amount of HCFC-225X is dehydrofluorinated. Here, the "minor amount" may, for example, be a case wherein the reaction amount of dehydrofluorination is generally less than 0.01 mol per 1 mol of HCFC-225X in the raw material mixture of HCFC-225 isomers, and preferably, such a reaction amount is 0 mol. However, practically, the reaction amount is determined by the proportion of HCFC-225X contained in HCFC-225.

In the concurrent production process of the present invention, by the operation of contacting the raw material composition with an alkali aqueous solution in the presence of a phase-transfer catalyst, the dehydrofluorination reaction represented by the above reaction formula (2) and the dehydrochlorination reaction represented by the above reaction formula (3) concurrently proceed in the same reactor. Hereinafter, these reactions may generally be referred to as a dehydrohalogenation reaction represented by the reaction formula (2)/(3).

(2-1) Alkali Aqueous Solution

The alkali aqueous solution to be used for the dehydrohalogenation reaction represented by the above reaction formula (2)/(3) is not particularly limited so long as it is an aqueous solution of a basic compound (alkali) capable of carrying out the above dehydrohalogenation reaction. Specifically, the reaction can be carried out by an aqueous solution of an inorganic basic compound such as an alkali metal hydroxide such as potassium hydroxide or sodium hydroxide, or an alkaline earth metal hydroxide such as calcium hydroxide, an organic basic compound such as an amine, or an alkali metal alkoxide. However, from the viewpoint of economical efficiency, it is preferred to use an aqueous-solution of an inorganic basic compound, and it is more preferred to use an aqueous solution of sodium hydroxide or potassium hydroxide from the viewpoint of the reaction activity and selectivity.

The alkali concentration of the alkali aqueous solution to be used for the above dehydrohalogenation reaction is preferably from 0.5 to 40 mass %, more preferably from 5 to 40 mass %, particularly preferably from 20 to 40 mass %, with a view to more selectively dehydrofluorinating HCFC-225ca in the mixture of HCFC-225 isomers in the raw material composition and at the same time accelerating the dehydrochlorination reaction of HCFC-244eb.

The amount of the alkali aqueous solution to be used for the dehydrohalogenation reaction represented by the above reaction formula (2)/(3) is not particularly limited so long as it is an amount capable of carrying out the above dehydrohalogenation reaction. However, it is preferably adjusted to be an alkali amount of from 0.5 to 1.5 mol equivalent, more preferably an alkali amount of from 1.0 to 1.3 mol equivalent, based on the components relating to the reaction in the raw material composition i.e. the total amount of HCFC-225ca and HCFC-244eb.

In the dehydrohalogenation reaction represented by the above reaction formula (2)/(3), the raw material composition subjected to the reaction and the above alkali aqueous solution to act thereon have no compatibility. Accordingly, to effectively carry out the contact of the two, in the process of the present invention, the reaction is carried out by using a phase-transfer catalyst which is soluble in water and in a water-insoluble organic solvent.

(2-2) Phase-Transfer Catalyst

As the phase-transfer catalyst to be used for the dehydrohalogenation reaction represented by the above formula (2)/(3) in the present invention, commonly employed phase-transfer catalysts may be mentioned without any particularly restriction. Specifically, a quaternary ammonium salt, a quaternary phosphonium salt, a quaternary arsonium salt, a sulfonium salt, a crown ether, etc. may be mentioned. Among them, a quaternary ammonium salt or a quaternary phosphonium salt is preferred.

As the quaternary ammonium salt, specifically, a compound represented by the following formula (i) (hereinafter referred to as the compound (i), as the case requires) may be mentioned.

(In the formula (i), each of $R^{11}$ to $R^{14}$ which are independent of one another, is a hydrocarbon group, and $Y^-$ is an anion.)

Here, in the above formula (1), $R^{11}$ to $R^{14}$ representing hydrocarbon groups are more specifically groups having the following characteristics.

As $R^{11}$ to $R^{14}$, an alkyl group, a cycloalkyl group, an alkenyl group, a cycloalkenyl group, an aryl group or the like may be mentioned, and an alkyl group or an aryl group is preferred.

The number of carbon atoms in $R^{11}$ to $R^{14}$ is preferably from 4 to 100 as the total number of carbon atoms per one molecule of $R^{11}R^{12}R^{13}R^{14}N^+$.

$R^{11}$ to $R^{14}$ may, respectively, be the same groups or different groups.

$R^{11}$ to $R^{14}$ may be substituted by a functional group which is inactive under the reaction conditions. Such an inactive functional group varies depending upon the reaction conditions, but a halogen atom, an ester group, a nitrile group, an acyl group, a carboxy group or an alkoxy group may, for example, be mentioned.

$R^{11}$ to $R^{14}$ may mutually be connected to form a heterocyclic ring such as a nitrogen-containing heterocyclic ring.

$R^{11}$ to $R^{14}$ may be a part of a polymer compound.

A quaternary ammonium ion $R^{11}R^{12}R^{13}R^{14}N^+$ having such $R^{11}$ to $R^{14}$ may specifically be e.g. a tetramethylammonium ion, a tetraethylammonium ion, a tetra-n-propylammonium ion, a tetra-n-butylammonium ion, a tri-n-octylmethylammonium ion, a cetyltrimethylammonium ion, a benzyltrimethylammonium ion, a benzyltriethylammonium ion, a cetylbenzyldimethylammonium ion, a cetylpyridinium ion, a n-dodecylpyridinium ion, a phenyltrimethylammonium ion, a phenyltriethylammonium ion, an N-benzylpicolinium ion, a pentamethonium ion or a hexamethonium ion.

Further, in the above formula (i), $Y^-$ representing an anion may specifically be e.g. a chlorine ion, a fluorine ion, a bromine ion, an iodine ion, a sulfate ion, a nitrate ion, a phosphate ion, a perchlorate ion, a hydrogensulfate ion, a hydroxy ion, an acetate ion, a benzoate ion, a benzenesulfonate ion, or a p-toluenesulfonate ion. A chlorine ion, a bromine ion, an iodine ion, a hydrogensulfate ion or a hydroxy ion is preferred.

Here, as the compound (i), a combination of the following $R^{11}R^{12}R^{13}R^{14}N^+$ and the following $Y^-$ is preferred from the viewpoint of the general versatility and reactivity of the compound (i).

$R^{11}R^{12}R^{13}R^{14}N^+$: A tetramethylammonium ion, a tetraethylammonium ion, a tetra-n-propylammonium ion, a tetra-n-butylammonium ion or a tri-n-octylmethylammonium ion.

$Y^-$: A fluorine ion, a chlorine ion or a bromine ion.

The above-mentioned quaternary phosphonium salt may specifically be a compound represented by the following formula (ii) (hereinafter referred to as the compound (ii) as the case requires).

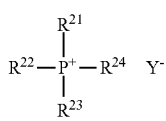

(ii)

(In the formula (ii), each of $R^{21}$ to $R^{24}$ which are independent of one another, is a hydrocarbon group, and $Y^-$ is an anion.)

Here, in the above formula (ii), $R^{21}$ to $R^{24}$ representing hydrocarbon groups are more specifically groups having the following characteristics.

As $R^{21}$ to $R^{24}$, an alkyl group, a cycloalkyl group, an alkenyl group, a cycloalkenyl group or an aryl group may, for example, be mentioned, and an alkyl group or an aryl group is preferred.

The number of carbon atoms in $R^{21}$ to $R^{24}$ is preferably from 4 to 100 as the total number of carbon atoms per one molecule of $R^{21}R^{22}R^{23}R^{24}P^+$.

$R^{21}$ to $R^{24}$ may, respectively, be the same groups or different groups.

$R^{21}$ to $R^{24}$ may be substituted by a functional group which is inactive under the reaction conditions. Such an inactive functional group varies depending upon the reaction conditions, but a halogen atom, an ester group, a nitrile group, an acyl group, a carboxy group or an alkoxy group may, for example, be mentioned.

A quaternary phosphonium ion $R^{21}R^{22}R^{23}R^{24}P^+$ having such $R^{21}$ to $R^{24}$ may specifically be e.g. a tetraethylphosphonium ion, a tetra-n-butylphosphonium ion, a tri-n-octylethylphosphonium ion, a cetyltriethylphosphonium ion, a cetyl-tri-n-butylphosphonium ion, a n-butyltriphenylphosphonium ion, a n-amyltriphenylphosphonium ion, a methyltriphenylphosphonium ion, a benzyltriphenylphosphonium or a tetraphenylphosphonium ion.

Further, in the above formula (ii), $Y^-$ representing an anion may specifically be e.g. a chlorine ion, a fluorine ion, a bromine ion, an iodine ion, a sulfate ion, a nitrate ion, a phosphate ion, a perchlorate ion, a hydrogensulfate ion, a hydroxy ion, an acetate ion, a benzoate ion, a benzenesulfonate ion or a p-toluenesulfonate ion, and a fluorine ion, a chlorine ion or a bromine ion is preferred.

Specific examples of the phase-transfer catalyst include tetramethylammonium chloride, tetraethylammonium bromide, tetra-n-propylammonium bromide, tetra-n-butylammonium bromide, tri-n-octylmethylammonium chloride, cetyltrimethylammonium bromide, benzyltrimethylammonium chloride, etc. Among them, tetra-n-butylammonium bromide is preferred from the viewpoint of the economical efficiency and safety.

The amount of the above phase-transfer catalyst is preferably from 0.001 to 1 part by mass, more preferably from 0.01 to 1 part by mass, per 100 parts by mass of the components subjected to the reaction in the raw material composition to be used i.e. the total of HCFC-225ca and HCFC-244eb.

(2-3) Dehydrohalogenation Reaction

Specifically, the dehydrohalogenation reaction represented by the above formula (2)/(3) is carried out by introducing the raw material composition, the above-described alkali aqueous solution and the phase-transfer catalyst in the above-described proportions into the reactor and carrying out stirring or the like by a usual means so that they are sufficiently contacted.

The reaction temperature in the above dehydrohalogenation reaction is not particularly limited, but from the viewpoint of the reaction activity and the selectivity for the desired product, it is preferably from 0 to 80° C. Further, the reaction temperature is suitably adjusted depending upon the pressure condition of the reactor during the reaction. For example, in a case where the dehydrohalogenation reaction is carried out under atmospheric pressure, the reaction is preferably carried out within a range of from 0 to 60° C., and with a view to more selectively dehydrofluorinating HCFC-225ca, the reaction is more preferably carried out within a range of from 0 to 20° C. Further, the above dehydrohalogenation reaction may be carried out in a pressurized reactor, and in such a case, from 98,000 to 200,000 Pa and from 50 to 80° C. may be mentioned as preferred conditions from the viewpoint of the conversion.

On the other hand, with a view to suppressing formation of byproducts by the dehydrofluorination reaction of HCFC-225X in the above-described HCFC-225 in the raw material composition, it is preferred to carry out the reaction within a temperature range of from 0 to 20° C.

The reaction represented by the above reaction formula (2)/(3) may be carried out by either a batch system or a continuous system, and the reaction time may suitably be adjusted depending upon the system by a usual method. Further, the material for the reactor to carry out this reaction may be a usual one such as glass, iron, nickel or an alloy containing such a metal as the main component.

According to the process of the present invention, after completion of the dehydrohalogenation reaction by the above reaction formula (2)/(3), the reaction solution is left to stand, whereby it is naturally separated into an organic phase and a water phase. In this organic phase, in addition to CFO-1214ya and HFO-1234yf, one or more isomers of HCFC-225 other than HCFC-225ca, not subjected to the dehydrofluorination reaction, may be contained. Further, in a case where as HCFC-244eb, a distillation residue obtained at the time of producing HFO-1234yf from CFO-1214ya is used, an unreacted raw material CFO-1214ya, an intermediate product HCFO-1224yd, etc. which are usually contained in such a distillation residue, may be contained.

Further, as mentioned above, depending upon the reaction conditions, a minor amount of isomers of CFO-1214ya formed by a slight dehydrofluorination reaction of HCFC-225 other than HCFC-225ca, e.g. 1,3-dichloro-1,2,3,3-tetrafluoropropene ($CClF_2CF=CClF$) formed by a dehydrofluorination reaction of HCFC-225cb (1,3-dichloro-1,2,2,3,3-pentafluoropropane, $CHClFCF_2CClF_2$), etc. may sometimes be contained in the above organic phase.

The amount of isomers of CFO-1214ya slightly present in this organic phase is a minor amount as mentioned above, which may be regarded as an amount at a level not influential over the conversion reaction to HFO-1234yf using CFO-1214ya or over the use as a refrigerant after the conversion. Further, the amount of isomers of CFO-1214ya contained in the organic phase is influenced by e.g. the reaction-conditions in the step of synthesizing HFO-1234yf by hydrogen reduction of CFO-1214ya, and is preferably at most 1,000 ppm as the amount to CFO-1214ya.

Here, CFO-1214ya, HFO-1234yf and HCFC-225 other than HCFC-225ca, in the above organic phase, respectively have suitable boiling point differences, and for example, the difference in boiling point between CFO-1214ya and HCFC-225 other than HCFC-225ca is about 10° C., which is within a range where separation and purification by usual distillation or the like are possible. Thus, CFO-1214ya and HFO-1234yf in the above organic phase can easily be separated and purified by a usual method and become useful for various applications.

Further, in a case where the above HCFO-1224yd is contained in the organic phase, in a usual distillation operation, HCFO-1224yd is separated in a state where it is contained in the distillate fraction of CFO-1214ya, but in a case where the distillate fraction of CFO-1214ya is used as a starting material for the following production of HFO-1234yf, HCFO-1224yd is an intermediate product at the time of producing HFO-1234yf from CFO-1214ya and thus can be used without a problem.

Further, if HCFC-225 (which may be only one compound) other than HCFC-225ca not subjected to the dehydrofluorination reaction, obtainable from the above organic phase, can be, although depend on the type of HCFC-225, isomerized by e.g. the above-mentioned catalytic reaction (U.S. Pat. No. 5,157,171) to obtain HCFC-225 including HCFC-225ca, which can be used as a part of the raw material for the concurrent production process of the present invention.

On the other hand, after completion of the dehydrohalogenation reaction by the above reaction formula (2)/(3), the water phase separated from the above organic phase may be taken out and can be re-used by adding an alkali to bring its concentration to a proper level again.

<Process for Producing HFO-1234yf>

The present invention also provides a process for producing HFO-1234yf, which comprises separating CFO-1214ya and HFO-1234yf, respectively, from the reaction product obtained by the above-described concurrent production process of present invention, and reacting the separated CFO-1214ya with hydrogen in the presence of a catalyst to produce HFO-1234yf. That is, a process is provided wherein HFO-1234yf is produced by using, as a starting material, CFO-1214ya being one of the compounds obtained by the above-described concurrent production process of the present invention, and together with HFO-1234yf being another compound obtained by the above-described concurrent process of the present invention, HFO-1234yf is produced. Now, the process for producing HFO-1234yf of the present invention will be described.

In this process, as the starting material, CFO-1214ya obtained by the above-described concurrent production process of the present invention is used, but the reaction raw material composition may contain an organic compound other than CFO-1214ya, within a range not to impair the reduction reaction of CFO-1214ya. As such an organic compound, the above HCFO-1224yd may, for example, be mentioned.

To produce HFO-1234yf by using CFO-1214ya obtained as described above, as shown by the following reaction formula (4), CFO-1214ya may be reacted with hydrogen in the presence of a catalyst.

[Reaction to form HFO-1234yf]

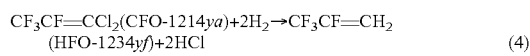

$$CF_3CF=CCl_2(CFO\text{-}1214ya)+2H_2 \rightarrow CF_3CF=CH_2 \\ (HFO\text{-}1234yf)+2HCl \quad (4)$$

The amount of hydrogen to be used for the reaction to form HFO-1234yf as shown by the above reaction formula (4) may specifically be usually from 0.5 to 10 mol, preferably from 0.5 to 5 mol, more preferably from 0.5 to 3 mol, per 1 mol of CFO-1214ya. When the amount of hydrogen is at least 0.5 mol per 1 mol of CFO-1214ya, the yield is particularly high, and no deterioration of the catalyst is likely to occur. Further, when it is at most 3 mol, a side reaction such as reduction or hydrogenation reaction of the desired product tends to scarcely occur, whereby the yield will be improved.

Further, the catalyst to be used for the reaction to form HFO-1234yf as represented by the above reaction formula (4) may, for example, be a palladium catalyst, or a metal mixture catalyst containing palladium as the main component and having added at least one member selected from a Group 10 element other than palladium, a Group 8 element, a Group 9 element and gold. As the above Group 10 element other than palladium, the Group 8 element and the Group 9 element, iron, cobalt, nickel, ruthenium, rhodium, iridium, osmium or platinum may be mentioned. Further, the amount of the metal other than palladium, is preferably from 0.01 to 50 parts by weight, per 100 parts by weight of palladium. Further, a complex catalyst having another metal added to palladium has such an effect that the durability of the catalyst becomes higher than one made of palladium alone.

The above palladium catalyst or the metal mixture catalyst containing palladium as the main component, is used as supported on a carrier. As such a carrier on which the catalyst is supported, it is possible to employ active carbon or a metal oxide such as alumina, zirconia or silica. Among them, active carbon is preferably employed from the viewpoint of the activity, durability and reaction selectivity. As such active carbon, one prepared from such a material as wood, charcoal, fruit shell, coconut shell, peat, lignite or coal may be used, but one obtained from a plant material rather than a mineral material is preferred, and particularly preferred is coconut shell active carbon. As the shape of the carrier, formed coal having a length of from about 2 to 5 mm, pulverized coal of from about 4 to 50 mesh or granulated coal may, for example, be used, but pulverized coal of from 4 to 20 mesh or formed coal is preferred.

For the reaction to form HFO-1234yf as represented by the above reaction formula (4), a gas phase reduction method is preferred wherein heated gaseous CFO-1214ya and hydrogen are passed in a reactor packed with the catalyst-supporting carrier and contacted with the catalyst at a temperature of from 130 to 250° C., preferably from 150 to 200° C. Further, in order to suppress formation of by-products, it is more preferred to use a gas phase reduction method wherein the reaction is carried out at a lower temperature. For example, it is preferred that using a raw material mixed gas containing CFO-1214ya and hydrogen, the temperature of the catalyst layer in the reactor packed with the catalyst-supporting carrier is adjusted to be at least the dew point of the raw material mixed gas, and while maintaining the temperature of the catalyst layer portion which rises by the reaction, to be lower than 130° C., the raw material mixed gas is passed through and reacted in the catalyst layer. The temperature of the catalyst layer in such a case may be lower than 50° C., but is preferably at least 50° C., more preferably at least 60° C. Whereas, the temperature of the catalyst layer at a portion where the temperature rises by the reaction, is preferably at most 100° C.

The reaction pressure is usually atmospheric pressure or spontaneous pressure, under which the reaction sufficiently proceeds. The contact time with the catalyst may be set within a range of usually from 4 to 60 seconds, preferably from 8 to 40 seconds. Further, in order to control the excessive rise of the temperature, the reaction may be carried out as diluted with an inert gas such as nitrogen.

The amount of an inert gas to be introduced is specifically usually at least 0.1 mol, preferably at least 0.5 mol, per 1 mol of CFO-1214ya. When the amount of the inert gas is at least 0.5 mol per 1 mol of CFO-1214ya, it is possible to suppress heat generation and to suppress formation of byproducts, whereby the yield can be made particularly high, and it is also possible to suppress deterioration of the catalyst. The upper limit is not particularly limited, but from the viewpoint of the recovery rate, the amount of the inert gas to be introduced is preferably at most 10 mol, particularly preferably at most 4 mol.

The material for the reactor to be used for the above reaction to form HFO-1234yf may, for example, be usual one such as glass, iron, nickel or an alloy containing such a metal as the main component.

For the recovery of HFO-1234yf as the reaction product and for the separation of unreacted substances, it is possible to employ a usual method, e.g. a common method such as distillation.

Here, as mentioned above, the distillation residue remaining after separation of HFO-1234yf by distillation from the reaction mixture obtained by the above reduction reaction of CFO-1214ya, contains an unreacted raw material CFO-1214ya, an intermediate product HCFO-1224yd and byproducts such as HCFC-244eb, etc. Such a distillation residue may be difficult to be recycled to the reduction reaction of CFO-1214ya due to the presence of HCFC-244eb, but it can be used as the raw material composition in the above-described concurrent production process of the present invention, and it can thereby be effectively recycled.

FIG. 1 shows an example of a production flowchart for producing HFO-1234yf via CFO-1214ya from HCFC-225ca, wherein the above process of the present invention is utilized. As is evident from this Fig., by using the process of the present invention, it is possible to produce HFO-1234yf useful as a new refrigerant by an economical process wherein the raw material compounds and byproducts are sufficiently recycled.

The present invention further provides a process for producing HFO-1234yf by a combination of various steps shown in FIG. 1. That is, the present invention further provides a process for producing HFO-1234yf, which comprises:

a hydrogenation step of reacting CFO-1214ya with hydrogen in the presence of a catalyst to produce HFO-1234yf, which is then separated from the reaction product, and to obtain a mixture comprising unreacted CFO-1214ya, HCFO-1224yd as an intermediate product, and HCFC-244eb as a by-product;

a mixing step of mixing dichloropentafluoropropane including HCFC-225ca and at least one of its isomers, and the mixture obtained in the above hydrogenation step to form a raw material composition comprising HCFC-225ca and HCFC-244eb; and a dehydrohalogenation step of contacting the above raw material composition with an alkali aqueous solution in the presence of a phase-transfer catalyst to produce CFO-1214ya from the above HCFC-225ca and to produce HFO-1234yf from the above HCFC-244eb, and separating the CFO-1214ya and the HFO-1234yf, respectively, from the reaction product;

wherein the CFO-1214ya separated in the above dehydrohalogenation step, is used as at least a part of CFO-1214ya in the above hydrogenation step.

In the above process for producing HFO-1234yf, it is further preferred to combine an isomerization step of isomerizing at least one HCFC-225 other than HCFC-225ca to HCFC-225ca.

That is, the above process for producing HFO-1234yf further includes an isomerization step of isomerizing at least one HCFC-225 other than HCFC-225ca, to HCFC-225ca, wherein in the above dehydrohalogenation step, at the same time as separating CFO-1214ya and HFO-1234yf, respectively, from the reaction product, dichloropentafluoropropane containing at least one dichloropentafluoropropane other than HCFC-225ca, is separated; the separated dichloropentafluoropropane is converted by the above isomerization step to dichloropentafluoropropane including HCFC-225ca and at least one of its isomers; and the dichloropentafluoropropane obtained in the above isomerization step is used as at least a part of dichloropentafluoropropane in the above mixing step.

EXAMPLES

Now, the present invention will be described in further detail with reference to Examples, but it should be understood that the present invention is by no means restricted by such specific Examples.

Example 1

Concurrent Production Example 1 for CFO-1214ya and HFO-1234yf

Into a glass reactor having an internal capacity of 10 L and provided with a Dimroth condenser cooled to 0° C., a dropping funnel and a stirrer, 3.88 g of tetra-n-butylammonium bromide (TBAB) as a phase-transfer catalyst and 7,750 g of a raw material composition comprising 50.41 mass % of HCFC-225ca, 5.14 mass % of HCFC-225cb, 0.52 mass % of HCFC-244eb, 38.89 mass % of CFO-1214ya and 4.9 mass % of HCFO-1224yd, were charged, and from the dropping funnel, 2,885 g of a 40 mass % potassium hydroxide aqueous solution was dropwise added over a period of about 3 hours, while controlling the dropping rate so that a reaction temperature of about 10° C. was maintained.

After the dropwise addition for about 3 hours, the reaction was continued for further 2 hours. Thereafter, a part of the organic phase was sampled and analyzed by gas chromatography (GC), whereby the conversions of HCFC-225ca and HCFC-244eb were 100% and 54%, and CFO-1214ya and HFO-1234yf were found to be formed.

Further, the reaction was continued for 15 hours, and as a result, the conversion of HCFC-244eb was improved to 80%. In this reaction, no reaction products from HCFC-225cb and HCFO-1224yd were observed.

Example 2

Production Example for HFO-1234yf

A catalyst-supporting carrier having 1.8 mass % of palladium and 0.2 mass % of gold supported on active carbon (tradename: Shirasagi C2X, manufactured by Takeda Pharmaceutical Company Limited), was packed in a reaction tube made of Inconel (registered trademark) 600 having an inner diameter of 2.54 cm and a length of 100 cm and immersed in a salt bath.

Using CFO-1214ya obtained in the above Example 1, a reduction reaction was carried out under the reaction conditions shown in the upper section in Table 1 to produce HFO-1234yf.

Confirmation of the reaction products was carried out by analyzing the outlet gas from the reactor by gas chromatography and calculating the crude gas molar composition. The results are shown in the lower section in Table 1.

TABLE 1

| Reaction conditions | Reaction temperature | 180° C. |
|---|---|---|
| | Raw material supply ratio: CFO-1214ya/H$_2$/N$_2$ | 1/2/3.4 (molar ratio) |
| | Contact time | 60 sec. |
| Crude gas | CF$_3$CF=CCl$_2$ (CFO-1214ya) | 30 mass % |

TABLE 1-continued

| composition | CF$_3$CF=CH$_2$ (HFO-1234yf) | 42 mass % |
|---|---|---|
| | HCFO-1224yd | 10 mass % |
| | HCFC-244eb | 0.4 mass % |

Example 3

Concurrent Production Example 2 for CFO-1214ya and HFO-1234yf

Into a glass reactor having an internal capacity of 1 L and provided with a Dimroth condenser cooled to 0° C., a dropping funnel and a stirrer, 0.36 g of tetra-n-butylammonium bromide (TBAB) as a phase-transfer catalyst and 700 g of raw material composition comprising 80.43 mass % of HCFC-225ca, 8.45 mass % of HCFC-225cb, 0.26 mass % of HCFC-244eb, 10.76 mass % of CFO-1214ya and 0.08 mass % of HCFO-1224yd, were charged, and from the dropping funnel, 413 g of a 40 mass % potassium hydroxide aqueous solution was dropwise added over a period of about 3 hours at a reaction temperature of from about 15° C. to 20° C.

Here, the above raw material composition is one prepared by adding HCFC-225cb and HCFC-225ca to a distillation residue obtained by distilling and removing HFO-1234yf by distillation purification of the crude product obtained in Example 2.

After the dropwise addition for about 3 hours, the reaction was continued for further 1 hour, whereupon the organic phase was analyzed by gas chromatography, whereby the conversions of HCFC-225ca and HCFC-244eb were 100% and 80%, and CFO-1214ya and HFO-1234yf were found to be formed.

Further, the reaction was continued for 19 hours, and as a result, the conversion of HCFC-244eb was found to be improved to 96%. In this reaction, no reaction products from HCFC-225cb and HCFO-1224yd were observed.

INDUSTRIAL APPLICABILITY

According to the process of the present invention, it is possible to produce CFO-1214ya simply and economically without requiring purification of the raw material component obtained as a mixture of isomers, i.e. HCFC-225ca, and at the same time to simply and economically produce HFO-1234yf useful as a new refrigerant from less useful HCFC-244eb.

Further, by using CFO-1214ya obtained by this process, it becomes possible to economically produce HFO-1234yf useful as a new refrigerant.

The entire disclosures of Japanese Patent Application No. 2010-142279 filed on Jun. 23, 2010 and U.S. Provisional Application No. 61/365,895 filed on Jul. 20, 2010 including specifications, claims and summaries are incorporated herein by reference in their entireties.

What is claimed is:

1. A process for producing tetrafluoropropenes, which comprises contacting a raw material composition comprising 1-chloro-2,3,3,3-tetrafluoropropane and dichloropentafluoropropane and 1,1-dichloro-2,2,3,3,3-pentafluoropropane and at least one of its isomers, with an alkali aqueous solution in the presence of a phase-transfer catalyst, to produce 1,1-dichloro-2,3,3,3-tetrafluoropropene from the 1,1-dichloro-2,3,3,3-pentafluoropropane and to produce 2,3,3,3-tetrafluoropropene from the 1-chloro-2,3,3,3-tetrafluoropropane, wherein the reaction amount of 1 mol of the isomer of 1,1-dichloro-2,2,3,3,3-pentafluoropropane to form an isomer of 1,1-dichloro-2,3,3,3-tetrafluoropropene is less than 0.01 mol.

2. The process according to claim 1, wherein the isomers of 1,1-dichloro-2,2,3,3,3-pentafluoropropane are 1,3-dichloro-1,2,2,3,3-pentafluoropropane, 2,2-dichloro-1,1,3,3,3-pentafluoropropane, 1,2-dichloro-1,2,3,3,3-pentafluoropropane and 2,3-dichloro-1,1,2,3,3-pentafluoropropane.

3. The process according to claim 1 or 2, wherein in the raw material composition, the proportion of 1,1-dichloro-2,2,3,3,3-pentafluoropropane in the dichloropentafluoropropane is at most 99.5 mol %.

4. The process according to claim 1 or 2, wherein the 1-chloro-2,3,3,3-tetrafluoropropane in the raw material composition is 1-chloro-2,3,3,3-tetrafluoropropane formed as a by-product in a reaction to produce 2,3,3,3-tetrafluoropropene by hydrolyzing 1,1-dichloro-2,3,3,3-tetrafluoropropene.

5. The process according to claim 1 or 2, wherein in the raw material composition, the amount of the 1-chloro-2,3,3,3-tetrafluoropropane is from 0.01 to 20 parts by mass to 100 parts by mass of the dichloropentafluoropropane.

6. The process according to claim 1 or 2, wherein the temperature for contacting the raw material composition with the alkali aqueous solution in the presence of a phase-transfer catalyst is from 0 to 20° C.

7. The process according to claim 1 or 2, wherein the alkali concentration in the alkali aqueous solution is from 0.5 to 40 mass %.

8. The process according to claim 1 or 2, wherein dichloropentafluoropropane is separated from the reaction product obtainable by the process according to claim 1 or claim 2; at least one of isomers other than 1,1-dichloro-2,2,3,3,3-pentafluoropropane in the separated dichloropentafluoropropane is isomerized to 1,1-dichloro-2,2,3,3,3-pentafluoropropane; and then, the dichloropentafluoropropane including 1,1-dichloro-2,2,3,3,3-pentafluoropropane obtained by the isomerization reaction is used as at least a part of the dichloropentafluoropropane in the raw material composition.

9. A process for producing 2,3,3,3-tetrafluoropropene, which comprises separating 1,1-dichloro-2,3,3,3-tetrafluoropropene and 2,3,3,3-tetrafluoropropene, respectively, from the reaction product obtainable by the process as defined in claim 1 or claim 2, and reacting the separated 1,1-dichloro-2,3,3,3-tetrafluoropropene with hydrogen in the presence of a catalyst to produce 2,3,3,3-tetrafluoropropene.

10. The process for producing 2,3,3,3-tetrafluoropropene according to claim 9, wherein from the hydrogenation reaction product, not only the 2,3,3,3-trafluoropropene is separated, but also a mixture comprising unreacted 1,1-dichloro-2,3,3,3-tetrafluoropropene, 1-chloro-2,3,3,3-tetrafluoropropene as an intermediate product and 1-chloro-2,3,3,3-tetrafluoropropane as a by-product, is separated; and the separated mixture is used as a part of the raw material composition in the process as defined in claim 1.

11. A process for producing 2,3,3,3-tetrafluoropropene, which comprises:
a hydrogenation step of reacting 1,1-dichloro-2,3,3,3-tetrafluoropropene with hydrogen in the presence of a catalyst to produce 2,3,3,3-tetrafluoropropene, which is separated from the reaction product, and to obtain a mixture comprising unreacted 1,1-dichloro-2,3,3,3-tetrafluoropropene, 1-chloro-2,3,3,3-tetrafluoropropene as an intermediate product and 1-chloro-2,3,3,3-tetrafluoropropane as a by-product;

a mixing step of mixing dichloropentafluoropropane including 1,1-dichloro-2,2,3,3,3-pentafluoropropane and at least one of its isomers, and the mixture obtained in the above hydrogenation step to obtain a raw material composition comprising 1,1-dilchloro-2,2,3,3,3-pentafluoropropane and 1-chloro-2,3,3,3-tetrafluoropropane; and a dehydrohalogenation step of contacting the raw material composition with an alkali aqueous solution in the presence of a phase-transfer catalyst to produce 1,1-dichloro-2,3,3,3-tetrafluoropropene from the 1,1-dichloro-2,2,3,3,3-pentafluoropropane and to produce 2,3,3,3-tetrafluoropropene from the 1-chloro-2,3,3,3-tetrafluoropropane, and separating the 1,1-dichloro-2,3,3,3-tetrafluoropene and the 2,3,3,3-tetrafluoropropene, respectively, from the reaction product;

wherein the 1,1-dichloro-2,3,3,3-tetrafluoropropene separated in the above dehydrohalogenation step is used as at least a part of the 1,1-dichloro-2,3,3,3-tetrafluoropropene in the above hydrogenation step, and wherein the reaction amount of 1 mol of the isomer of 1,1-dichloro-2,2,3,3,3-pentafluoropropane to form an isomer of 1,1-dichloro-2,3,3,3-tetrafluoropropene is less than 0.01 mol.

12. The process for producing 2,3,3,3-tetrafluoropropene according to claim 11, which further contains an isomerization step of isomerizing at least one of dichloropentafluoropropane other than 1,1-dichloro-2,2,3,3,3-pentafluoropropane to 1,1-dichloro-2,2,3,3,3-pentafluoropropane, wherein in the dehydrohalogenation step, from the reaction product, not only the 1,1-dichloro-2,3,3,3-tetrafluoropropene and the 2,3,3,3-tetrafluoropropene are, respectively, separated, but also dichloropentafluoropropane including at least one of dichloropentafluoropropane other than 1,1-dichloro-2,2,3,3,3-pentafluoropropane, is separated; the separated dichloropentafluoropropane is converted, by the isomerization step, to dichloropentafluoropropane including 1,1-dichloro-2,2,3,3,3-pentafluoropropane and at least one of its isomers; and the dichloropentafluoropropane obtained in the isomerization step is used as at least a part of the dichloropentafluoropropane in the above mixing step.

* * * * *

UNITED STATES PATENT AND TRADEMARK OFFICE
CERTIFICATE OF CORRECTION

PATENT NO. : 8,642,820 B2
APPLICATION NO. : 13/167285
DATED : February 4, 2014
INVENTOR(S) : Ryuji Seki et al.

It is certified that error appears in the above-identified patent and that said Letters Patent is hereby corrected as shown below:

On the title page, Item (54) and in the Specification, Column 1, the Title is incorrect. Item (54) and Column 1 should read:

--PROCESS FOR PRODUCING 1,1-DICHLORO-2,3,3,3-TETRAFLUOROPROPENE AND 2,3,3,3-TETRAFLUOROPROPENE--

Signed and Sealed this
Twenty-second Day of April, 2014

Michelle K. Lee
*Deputy Director of the United States Patent and Trademark Office*